(12) United States Patent
Cronin

(10) Patent No.: US 9,161,811 B2
(45) Date of Patent: Oct. 20, 2015

(54) RADIATION APPLICATOR FOR MICROWAVE MEDICAL TREATMENT

(71) Applicant: AngioDynamics, Inc., Latham, NY (US)

(72) Inventor: Nigel Cronin, Lane Bath (GB)

(73) Assignee: AngioDynamics, Inc., Latham, NY (US)

(*) Notice: Subject to any disclaimer, the term of this patent is extended or adjusted under 35 U.S.C. 154(b) by 51 days.

(21) Appl. No.: 13/683,047

(22) Filed: Nov. 21, 2012

(65) Prior Publication Data

US 2013/0267941 A1     Oct. 10, 2013

Related U.S. Application Data

(63) Continuation of application No. 10/561,701, filed on Aug. 9, 2006, now abandoned.

(51) Int. Cl.
*A61B 18/18* (2006.01)

(52) U.S. Cl.
CPC ............. *A61B 18/18* (2013.01); *A61B 18/1815* (2013.01)

(58) Field of Classification Search
CPC ............... A61B 18/1815; A61B 18/18; A61B 2018/1869; A61B 2018/00702; A61N 5/02
USPC ............ 606/32, 33, 41; 607/96, 98, 100, 101, 607/154–6
See application file for complete search history.

(56) References Cited

U.S. PATENT DOCUMENTS

| | | | | |
|---|---|---|---|---|
| 6,287,302 B1 * | 9/2001 | Berube | | 606/33 |
| 6,723,094 B1 * | 4/2004 | Desinger | | 606/50 |
| 2003/0109862 A1 * | 6/2003 | Prakash et al. | | 606/33 |
| 2004/0215185 A1 * | 10/2004 | Truckai et al. | | 606/41 |

* cited by examiner

*Primary Examiner* — Aaron Roane
(74) *Attorney, Agent, or Firm* — Peter J. Flora

(57) ABSTRACT

A radiation applicator with a dielectric body (2) surrounding the antenna. The dielectric body (2) is comprised of three sections (3, 4 and 5) with different dielectric constants to provide broad-band matching of the applicator to surrounding material. Washers (10) and (11) are mounted on the antenna to act as reflectors.

6 Claims, 2 Drawing Sheets

RADIATION APPLICATOR FOR MICROWAVE MEDICAL TREATMENT

This application is a continuation of U.S. application Ser. No. 10/561,701, filed on Aug. 9, 2006, which application is a 371 of PCT/GB04/002620, filed Jun. 18, 2004, which claims the benefit of priority application United Kingdom 0314631.3, filed Jun. 18, 2003. This invention relates to radiation applicators and, in particular, to microwave medical treatment devices.

TECHNICAL FIELD

1. Prior Art

A known radiation applicator used for microwave medical treatment is shown in PCT/GB00/00682 and comprises a generator which supplies microwave energy via a coaxial conductor to a tip region at the distal end of the conductor. Dielectric packing is provided between the inner and outer conductors of the coaxial conductor but a length of the inner conductor at the tip projects beyond the outer conductor so as to form an antenna to emit radiation. The antenna is embedded axially in a cylindrical body of dielectric which has the same outer diameter as the coaxial conductor. A pointed tip at the end of the dielectric body serves to assist penetration into biological matter, such as a liver to perform ablation on a tumour.

2. Disclosure of the Invention

According to one aspect of the invention, a radiation applicator has a power input at one end, an elongate antenna extending axially at its distal end for emitting radiation into surrounding material, and a dielectric body which surrounds the antenna, characterised in that the dielectric body consists of multiple sections of different dielectric constant which are located axially relative to one another along the antenna.

The dielectric constant of each section of the dielectric body is selected so as to tune the applicator to operate at a particular frequency or range of frequencies for optimum performance in transferring energy to the surrounding material of predetermined dielectric constant. For example, energy transfer from the applicator to the surrounding material may change the physical properties of that material and the sectioned nature of the dielectric body may, in some embodiments, permit a broadband match of the applicator to the surrounding material so as to allow efficient energy transfer to the material to continue despite changes in the properties of the material.

Preferably, the dielectric body consists of three consecutive sections: a first section adjacent the power unit, a second first section adapted to be the major emitter of radiation, and a third tipsection. The second section has a higher dielectric constant than the first section. The higher dielectric constant of the second section allows the overall length of the dielectric body to be made shorter than would otherwise be required if the dielectric body was composed entirely of the material of the first dielectric, the length being related to the wavelength of the radiation in the dielectric. The third, tip section, is composed entirely of a material with a dielectric value from the other two sections and is chosen as a match to the surrounding material. The use of multiple sections of different dielectric constant allows the reflections from the dielectric interfaces to be used for matching or turning at the power input to ensure optimum power transfer.

Preferably, the dielectric body has a tip section furthest from the power input which is pointed so as to penetrate the surrounding material in use. The fact that the tip is composed of a dielectric material and not an electrical conductor serves to avoid local surface heating. Preferably, the dielectric constant of the tip is less than that of the second section, and is preferably intermediate that of the first and second sections.

The multiple sections could be made as an integral body, or made as separate components assembled together to abut against one another end-to-end.

According to a further feature of the invention, a radiation reflector is provided at the interface between sections of the dielectric body so as to modulate the transmission of radiation and further tune the applicator. Preferably, a radiation reflector is provided each side of the section which is intended to emit radiation into the surrounding material, a reflector on that side further from the input end having a larger area so as to reflect more energy than the reflector nearer the input end, thereby reducing transmission of radiation to the tip of the applicator. The emission of radiation from the dielectric body can therefore be more localised in one section. Preferably, the invention is designed to radiate more energy from the second section.

According to a second aspect of the invention, a radiation applicator has a power input at one end, an elongate antenna extending axially at its distal end for emitting radiation into surrounding material, and a dielectric body which surrounds the antenna, characterised in that one or more radiation reflectors are located axially along the antenna within the dielectric body to modulate the transmission of radiation.

Preferably, two radiation reflectors are spaced apart with the intermediate section of the dielectric body being intended to emit radiation into the surrounding material, the reflector on one side further from the input having a larger area so as to reflect more radiation than the reflector nearer the input end, thereby reducing transmission of radiation to the tip of the applicator.

Preferably, the reflectors, as used in connection with either the first or second aspect of the invention, are located at the interface between separate abutting sections of the dielectric body and help give structural support to the applicator. For example, the reflectors can be soldered or otherwise bonded to sections of the dielectric body and antenna.

DESCRIPTION OF THE DRAWINGS

The invention will now be described by way of example with reference to the accompanying drawings in which.

EMBODIMENTS OF THE INVENTION

Figure 1:
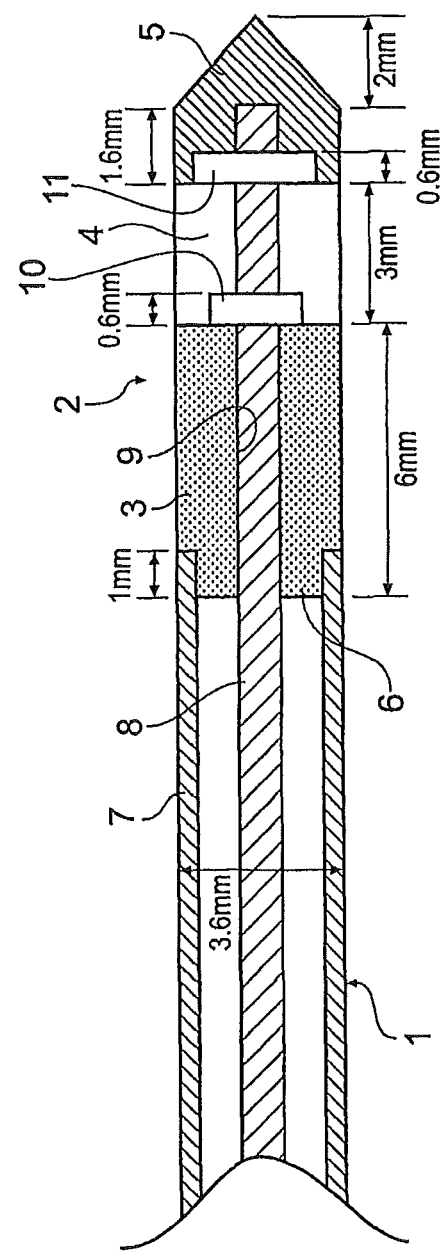
FIG. 1 shows an axially section through the tip of the radiation applicator according to the invention.

The radiation applicator illustrated in FIG. 1 comprises a coaxial conductor 1, which may be rigid or flexible, and which is connected to a microwave power supply at one end (not shown) and terminates at its other end in a radiation emitting tip 2. The tip 2 consists of a cylindrical dielectric body composed of three sections 3,4,5, coaxially aligned and abutting one another at interfaces between them so as to form a continuous body. One outer section 3 is connected to the end of the coaxial conductor 1. A portion 6 of the section 3 at one end is of reduced diameter and is inserted a short distance into the outer conductor 7 of the coaxial conductor to make a secure connection. The central conductor 8 of the coaxial conductor extends through an axial hole 9 in the body 2, through all three sections but terminating within the outer third section 5. During assembly, a metal washer 10 is soldered to the section 3 at the interface with section 4, and is soldered to the central conductor 8; and a second metal washer 11 is soldered to the middle section 4 at the interface with the third section 5, and is soldered to the central conductor 8. The washers 10 and 11 therefore serve to secure the two sections 3 and 4 of the dielectric body to the end of the coaxial conductor 1 via the central conductor 8. The third section 5 is then bonded to the second washer 11 and central conductor 8.

The third section 5 of the applicator has a pointed shape to assist insertion into material to be treated, and this will be made as sharp as is necessary for the application, for example, the treatment of liver cancer.

In operation, that portion of the central conductor 8 that extends from the outer conductor 7, acts as an antenna to emit radiation. The wavelength of the radiation within the dielectric body is determined by the frequency of the power supply and the dielectric constant of the various components. Thus the wavelength of the radiation is different in each of the three sections 3, 4 and 5. By appropriate selection of the dielectric constant of these three sections relative to one another and to the surrounding material in which the applicator is to be used, it is possible to tune the applicator to give optimum performance.

Another factor which affects the tuning of the applicator is the metal gaskets 10 and 11 which act as radiation reflectors. Both gaskets serve to reflect radiation back to the input, and with appropriate matching at the input ensures a maximum transfer of energy to the tip 2. The gasket 11 has a larger surface area than the gasket 10 so as to reduce the amount of energy transmitted to the third section 5.

Other factors which affect tuning are the length of the central conductor 8 extending beyond the outer conductor 7, the diameter and axial length of the individual dielectric sections 3, 4 and 5, and the thickness and diameter of the washers 10,11.

It will be appreciated that the choice of dielectric materials and dimensions of the various components allows great flexibility in designing a radiation applicator to suit a wide range of applications and performance requirements, bearing in mind that the dielectric constant of the surrounding material when the device is in use, will effect performance.

For example, a radiation applicator designed for medical use has the dimensions shown in FIG. 1 and the following further specifications: the washer 10 has an outer diameter of 1.9 mm; the washer 11 has an outer diameter of 2.7 mm; the central conductor 8 protrudes beyond the outer conductor by 8.5 mm; and the dielectric sections 3,4,5 are composed, respectively, of alumina with dielectric constant 10, titanium oxide with dielectric constant 100 and a Ca—Ti—Nd—Al dielectric with dielectric constant 47. The applicator of this example is capable of operating well at frequencies in the vicinity of 3 GHz. In particular, the applicator of this example is especially suited to operation at a frequency of 2.45 GHz and a power of 50 W.

Figure 2:
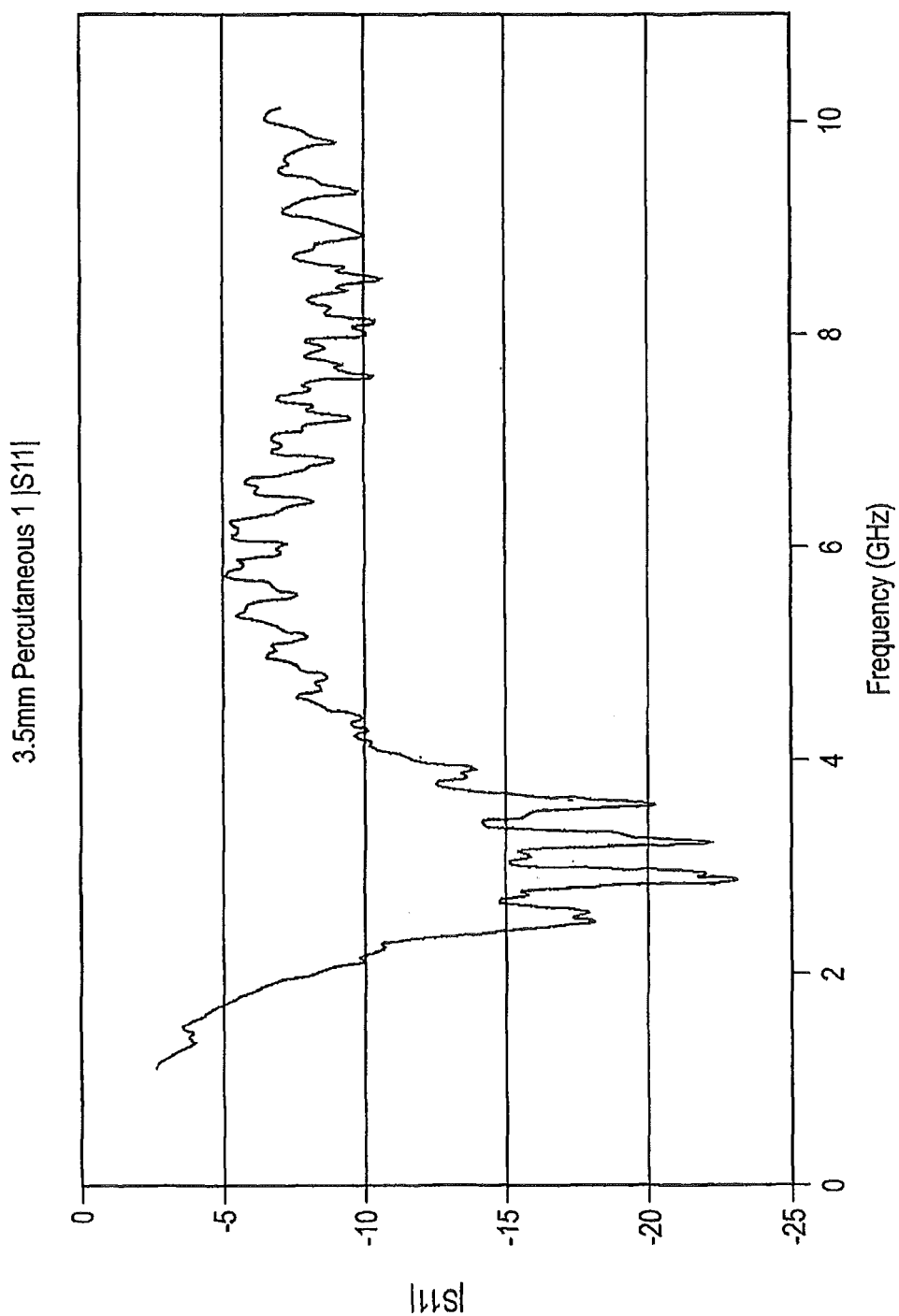
FIG. 2 shows a graph of reflected radiation at the input of the radiation applicator of FIG. 1 against the input frequency.

The performance of the applicator of the above example is illustrated in FIG. 2. This shows the power reflected from the tip of the applicator against the operating frequency, and shows that there is a dip in the reflected power at about 2.45 GHz, which corresponds to a maximum transfer of energy to the tip at this frequency. The width of the dip in FIG. 2, which is about 0.6 GHz, gives the applicator a broadband characteristic which allows it to better accommodate use with surrounding materials with a range of dielectric constant values.

In alternative embodiments of the invention, other dielectric materials may be used, including air, and instead of three dielectric sections there may be just two or may be four or more. Grooves may be formed in the outer surface of each or any of the dielectric section circumferentially. Also, the dielectric sections may be tapered longitudinally.

Also, an imaging process could be used to guide the applicator to the desired location. The applicator may be of small enough diameter to be inserted through a guidewire, such as used in ultrasound imaging techniques, so as to ensure accurate treatment in use.

The invention claimed is:

1. An applicator having an antenna for emitting microwave energy comprising:
    an outer conductor having a proximal end and a distal end;
    an inner conductor having a proximal end and a distal end;
    a first dielectric body having a proximal end and a distal end, the first dielectric body is comprised of a first dielectric material having a first dielectric constant, the proximal end of the first dielectric, body extends coaxially within the outer conductor;
    a second dielectric body having a proximal end and a distal end, the second dielectric body is comprised of a second dielectric material having a second dielectric constant, the second dielectric body has a sharp end capable of piecing through tissue, the second dielectric body having a cavity;
    a tuning reflector having a proximal end and a distal end, the distal most end and the proximal most end of the tuning reflector are both inside the cavity of the second dielectric body, the tuning reflector is comprised of a third dielectric material having a third dielectric constant; and
    the first dielectric constant, the second dielectric constant, and the third dielectric constant are different.

2. The applicator of claim 1, wherein the tuning reflector is directly connected to the distal end of the inner conductor.

3. The applicator of claim 2, wherein the tuning reflector is soldered to the inner conductor.

4. The applicator of claim 1 further comprising the applicator having a maximum transfer of energy to the second dielectric body at a frequency of about 2.45 GHz.

5. The applicator of claim 1 further comprising a third dielectric body between the inner conductor and outer conductor having a fourth dielectric constant.

6. The applicator of claim 1, wherein the proximal end of the first dielectric body is tapered.

* * * * *